United States Patent [19]

Crossley et al.

[11] 4,105,773

[45] Aug. 8, 1978

[54] 4-AMIDO-2-ALKOXY THIAZOLES AND COMPOSITION

[75] Inventors: Roger Crossley, Reading; David George Hill, Cookham, both of United Kingdom

[73] Assignee: John Wyeth & Brother Limited, Maidenhead, England

[21] Appl. No.: 799,820

[22] Filed: May 23, 1977

[30] Foreign Application Priority Data

Jun. 10, 1976 [GB] United Kingdom ............... 24162/76

[51] Int. Cl.$^2$ ................... A61K 31/425; C07D 277/02
[52] U.S. Cl. ............................. 424/270; 260/306.8 R
[58] Field of Search ................... 260/306.8 R; 424/270

[56] References Cited

U.S. PATENT DOCUMENTS

| 3,244,723 | 4/1966 | Johnson et al. | 260/306.8 R |
| 3,939,172 | 2/1976 | Gallagher et al. | 260/306.8 R |

Primary Examiner—Nicholas S. Rizzo
Attorney, Agent, or Firm—Arthur E. Wilfond

[57] ABSTRACT

The invention provides a compound of formula I,

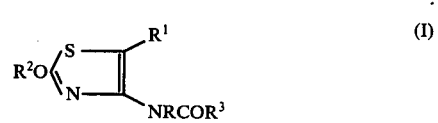

wherein R is hydrogen, alkyl of 1-6 carbon atoms, or $COR^3$ where $R^3$ is hydrogen, alkyl of 1-5 carbon atoms, alkenyl of 2 to 5 carbon atoms, alkynyl of 2 to 5 carbon atoms, or cycloalkyl of 3 to 5 carbon atoms, $R^1$ is hydrogen or alkyl of 1-6 carbon atoms, $R^2$ is alkyl of 1-6 carbon atoms and $R^3$ is as above defined.

The compounds are intended for use in the treatment of ulcers or hypersecretion in mammals.

12 Claims, No Drawings

4-AMIDO-2-ALKOXY THIAZOLES AND COMPOSITION

The invention relates to novel compounds with anti-ulcer or anti-secretory activity, pharmaceutical compositions containing the same and methods of treating ulcers.

The present invention provides a compound of formula I

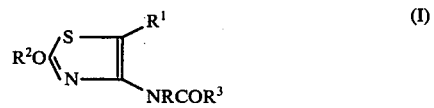

wherein R is hydrogen, alkyl of 1–6 carbon atoms or $COR^3$ where $R^3$ is hydrogen, alkyl of 1–5 carbon atoms (which may be substituted by one or more of the following: chlorine, bromine, trifluoromethyl, methoxy, ethoxy, amino, loweralkylamino, diloweralkylamino, hydroxy or cyano), alkenyl of 2 to 5 carbon atoms, alkynyl of 2 to 5 carbon atoms, perfluoroalkyl of 1–5 carbon atoms, cycloalkyl of 3 to 5 carbon atoms, $R^1$ is hydrogen or alkyl of 1–6 carbon atoms, $R^2$ is alkyl of 1–6 carbon atoms.

In the compounds of formula I, examples of alkyl for R, $R^1$, $R^2$ and $R^3$ are methyl, ethyl, n-propyl, isopropyl or n-butyl; for the alkenyl group $R^3$ vinyl, prop-1-enyl, but-1-enyl, but-2-enyl; for the alkynyl group $R^3$ ethynyl, prop-2-ynyl, but-2-ynyl; for the cyclo alkyl group $R^3$ cyclopropyl, cyclobutyl and cyclopentyl, for the perfluoroalkyl group $R^3$ trifluoromethyl and pentafluoroethyl.

When the term "lower alkyl" is used in this specification either alone or as part of another radical it means an alkyl group of 1–6 carbon atoms which may have a straight or branched chain e.g. methyl, ethyl, n-propyl, iso-propyl, n-butyl, s-butyl, t-butyl, n-pentyl, or n-hexyl.

Preferred examples of lower-alkyl-amino are methylamino and ethylamino. Examples of diloweralkylamino are dimethylamino and diethylamino.

$R^1$ when alkyl of 1–6 carbon atoms may be any of the lower alkyl radicals discussed above but is preferably methyl or ethyl.

The compounds of formula I are anti-ulcer agents which possess activity in the stress-induced erosion test of Senay & Levine, Proc.Soc.Exp.Biol.Med., 124, 1221-3 (1967) or anti-secretory activity in the test of H. Shay, D. Sun and H. Greenstein, Gastroenterology, 1954, 26, 903-13. The compounds which possess one or both these activities are considered to be anti-ulcer agents.

The invention includes a pharmaceutical composition comprising an effective amount of a compound of formula I and a pharmaceutically acceptable carrier.

Preferably the pharmaceutical composition is in unit dosage form e.g. as tablets or capsules.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 25mg. or less to 500 mg or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminium glycinate, calcium carbonate magnesium trisilicate, sodium bicarbonate or the alumina gel described in British Specification No. 1,284,394.

The preferred compounds of formula I used in the pharmaceutical compositions of the invention are those in which $R^2$ is methyl, R is hydrogen or $COR^3$ and $R^3$ is hydrogen or methyl. Preferably $R^1$ is hydrogen or methyl.

The invention includes methods of preparing the compounds of formula I. Thus compounds of formula I may be prepared by treatment of the corresponding 2-halo thiazoles of formula II

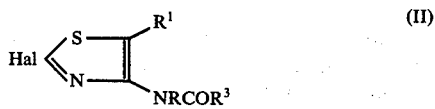

where Hal is chlorine or bromine and $R^1$, R and $R^3$ are as defined in connection with formula I with an alkali-metal alkoxide $R^2OM$ where M is an alkali-metal e.g. sodium, potassium or lithium and $R^2$ is alkyl of 1–6 carbon atoms. It is important that the alkali-metal alkoxide should be free of alkali-metal hydroxide residue. This may be achieved by preparing the alkoxide from the dry alkanol and taking precautions to keep the alkoxide dry.

Alternatively a compound of formula III

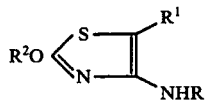  (III)

where $R^2$, $R^1$ and R are as defined in connection with formula I, may be acylated. This method may be used to prepare both mono and diacyl-amino compounds.

Standard acylating agents capable of introducing the group $R^3CO$ may be used e.g. the acid chloride $R^3COCl$, acid anhydride

or mixed anhydride

where $R^3$ is as defined above and $R^4$ is another $R^3$ group.

When the group $R^3CO$ is formyl, formylation may be achieved by use of the mixed anhydride of formic acid and acetic acid which can be produced from formic acid in acetic anhydride.

When the group $R^3$ is alkyl carrying a substituent functional group then one such group may be converted to another by standard methods.

The starting compounds of formula II wherein Hal is Bromine are described in J. Org. Chem., 1963, 28, 1877-83 or may be prepared by analogous methods. The compounds of formula II where Hal is chlorine may be prepared by methods described by Erlenmeyer et al Helv.Chim.Acta, 29, 1229-31.

Starting compounds of formula III where R is $COR^3$ may be prepared by acylation of the corresponding compounds where R is hydrogen.

Compounds of formula I may also be prepared by Curtius rearrangement of a thiazole ester of formula (IV)

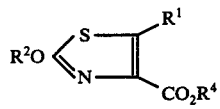  (IV)

where $R^1$ and $R^2$ are as defined in connection with formula I and $R^4$ is lower alkyl.

The ester of formula (IV) is treated with hydrazine to give the hydrazide of formula (V)

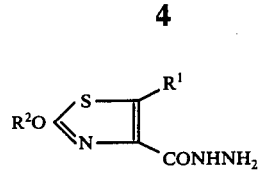  (V)

followed by nitrous acid to give the carbonyl azide of formula (VI)

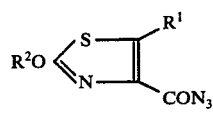  (VI)

The azide (VI) may then be rearranged with an acid anhydride or mixed anhydride to give a compound of formula I wherein R is hydrogen and $R^3$ is as defined in connection with formula I. The invention includes the above method and in particular the method of treating an azide of formula (VI) wherein $R^1$ and $R^2$ are as defined in connection with formula I with an acid anhydride of formula

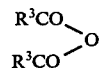

or a mixed anhydride of formula

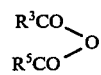

wherein $R^3$ is as defined in connection with formula I and $R^5CO$ is the residue of another acid.

A further method for preparing the compounds of formula I, wherein R is hydrogen and $R^3$ is other than hydrogen comprises carrying out a Beckmann rearrangement of an oxime of formula (VII)

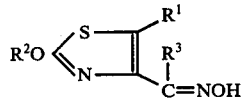  (VII)

wherein $R^1$ and $R^2$ are as defined in connection with formula I and $R^3$ is as defined in connection with formula I, except hydrogen.

The rearrangement is carried out under standard conditions for the Beckmann rearrangement e.g. phosphorus pentachloride in ether.

The starting compounds of formula VII may be prepared by known methods e.g. by reaction of a thioamide (VIII) with an oxime (IX).

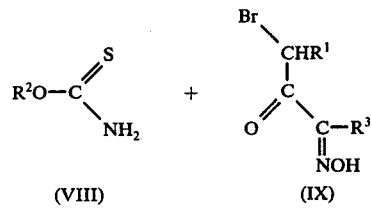

(VIII)    (IX)

In formulae VIII and IX $R^1$ and $R^2$ are as defined in connection with formula I and $R^3$ is as defined in connection with formula I except hydrogen.

A further method of preparing compounds of formula I comprises alkylating a corresponding 2-hydroxythiazole of formula X with a diazoalkane $R^6N_2$

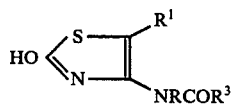

$R^1$ and $R^3$ are as defined in connection with formula I and $R^6$ is an alkyl residue capable of providing the group $R^2$ i.e. a group $C_nH_{2n}$ where $n$ is an integer from 1 to 6.

Compounds of formula I in which R is lower alkyl of 1–6 carbon atoms may also be prepared by alkylation of corresponding compounds of formula I wherein R is hydrogen. The alkylation may be carried out, for example, by treatment of a compound of formula I wherein R is hydrogen with an alkali metal hydride (e.g. sodium hydride) or equivalent base and an alkylating agent (such as a di(loweralkyl) sulphate, alkyl tosylate or a lower alkyl halide).

Pharmacological Test Results

When tested orally in rats 4-acetamido-2-methoxythiazole showed good activity at 100 and 30 mpk in the test of Senay & Levine mentioned above. The compound displayed outstandingly good anti-secretory activity in the test of Shay et al at 30 mpk but was inactive at 10 mpk.

| Compound | Stress-induced erosion (Senay & Levine) | | Anti-secretory (Shay et al) | | | | |
|---|---|---|---|---|---|---|---|
| | mpk p.o. | % Inhib | mpk ID | Vol | Conc | Free $H^+$ | Total $H^+$ |
| 4-acetamido-2-methoxythiazole | 100 | 72 | 30 | −80% | Insuff. gastric juice for titration | | |
| | 30 | 82 | 10 | NS | | | |

NS = Not Significant

The invention also includes a method of treating ulcers or hypersecretion in an afflicted mammal which method comprises administering to said mammal an effective amount of a compound of formula I as defined above. The dose will be varied according to the activity of the compound. For a compound such as 4-acetamido-2-methoxythiazole the amount of active ingredient may be from 10 to 100 mg/kg.

Preferably the compound used is 4-acetamido-2-methoxythiazole.

The following examples illustrate pharmaceutical compositions in accordance with the invention.

EXAMPLE A

| Suspension | % w/v |
|---|---|
| Aluminium hydroxide gel B.P. 5% $Al_2O_3$ | 80% = 4% $Al_2O_3$ |
| Magnesia Magma 12% w/v MgO | 10% |
| 4-acetamido-2-methoxythiazole | 2.0% |
| Glycerin B.P. | 3.0% |
| Alcohol 60 O.P.* | 0.08 |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00% |

*O.P. denotes overproof. 60 O.P. represents 91% w/v Ethanol/Water.

The above suspension is prepared by the following procedure. Add to the Alumina gel Magnesia Magma followed by the thiazole dispersed in glycerin, the peppermint oil dissolved in alcohol, the saccharin sodium dissolved in water, and the p-hydroxybenzoates dissolved in water. Make up to volume of water and stir well. Dose: 5 ml. t.d.s.

EXAMPLE B

| Antacid Tablet (chewable) | |
|---|---|
| Saccharin | 1.0 mg. |
| Hydrated alumina sucrose powder | 750.0 mg. |
| 4-acetamido-2-methoxythiazole | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE C

| Anti-ulcer tablet (without antacid) | mg/tablet |
|---|---|
| 4-acetamido-2-methoxythiazole | 100 mg. |
| Celutab | 147.5 mg. |
| Mag. Stearate | 2.5 mg. |
| | 250.0 mg. |

The tablets are prepared by the following method.

Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallised.

Further pharmaceutical compositions may be prepared by replacing 4-acetamido-2-methoxythiazole in any of Examples A to C with another thiazole of the invention e.g. one of the thiazoles of Examples 2–5 below.

The compounds of the invention are further illustrated by the following examples.

EXAMPLE 1

4-Acetamido-2-methoxy-thiazole

A solution of 4-acetamido-2-bromothiazole (15g) and sodium (3g) in "absolute methanol" was refluxed for 3 days. The reaction mixture was cooled and the solvent removed in vacuo. The residue was purified by column chromatography using silica gel and eluting with ethyl acetate and recrystallised from di-isopropyl ether to give the title compound (1g) m.p. 133–4° (Found: C, 42.2; H, 4.7; N, 16.4. $C_6H_8N_2O_2S$ requires C, 41.9; H, 4.7; N, 16.3%).

EXAMPLE 2

4-Acetamido-2-ethoxy-thiazole

Following the procedure of Example 1 4-acetamido-2-bromothiazole is treated with sodium in absolute ethanol to give the title compound.

EXAMPLE 3

4-Acetamido-2-methoxy-5-methylthiazole

4-Acetamido-2-bromo-5-methylthiazole (prepared by acylating 4-amino-2-bromo-5-methylthiazole with acetic anhydride) is treated with sodium in absolute methanol as described in Example 1 to give the title compound.

EXAMPLE 4

4-Diacetylamino-2-methoxythiazole

4-Diacetylamino-2-methoxythiazole may be prepared by acylating 4-acetylamino-2-methoxythiazole with acetic anhydride.

EXAMPLE 5

4-Acrylamido-2-methoxythiazole

4-Amino-2-bromothiazole is treated with acryloylchloride to give 4-acrylamido-2-bromothiazole which is refluxed with sodium in absolute methanol for sufficient time to produce the title compound.

EXAMPLE 6

2-Methoxy-4-(N-methylacetamido)thiazole

A solution of 4-acetamido-2-bromothiazole and methyl tosylate (4.65 g, 25 mM) in dry acetonitrile (125 ml) was treated with a 60% dispersion of sodium hydride in oil (1 g, 25 mM) and the mixture stirred 72 hours at ambient temperature. The reaction mixture was filtered and the filtrate evaporated under reduced pressure. The residue was chromatographed on silica (Woelm grade 1, 150 g) using 2% methanol in chloroform as eluant. Evaporations of the appropriate fractions followed by recrystallisation from hexane gave 2-bromo-4-(N-methylacetamido)thiazole (1.9 g, 32%) mp 84° C. Found: C, 30.55; H, 2.95; N, 11.8%, $C_6H_7N_2BrOS$ requires C, 30.7; H, 3.0; N, 11.9%).

2-Bromo-4-(N-methylacetamido)thiazole is treated with sodium in absolute methanol following the procedure described in Example 1 to give the title compound.

We claim:
1. A compound of formula I,

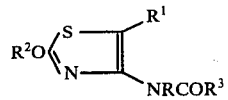

wherein R is hydrogen, alkyl of 1–6 carbon atoms, or $COR^3$ where $R^3$ is hydrogen, alkyl of 1–5 carbon atoms, alkenyl of 2 to 5 carbon atoms, alkynyl of 2 to 5 carbon atoms, or cycloalkyl of 3 to 5 carbon atoms, $R^1$ is hydrogen or alkyl of 1–6 carbon atoms, $R^2$ is alkyl of 1–6 carbon atoms and $R^3$ is as above defined.

2. A compound as claimed in claim 1, wherein $R^1$ is hydrogen or alkyl of 1–6 carbon atoms, $R^2$ is alkyl of 1–6 carbon atoms, $R^3$ is hydrogen or alkyl of 1–5 carbon atoms and R is hydrogen, alkyl of 1–6 carbon atoms or $COR^3$ where $R^3$ is as defined above.

3. A compound as claimed in claim 1, wherein $R^1$ is hydrogen or alkyl of 1–6 carbon atoms, $R^2$ is alkyl of 1–6 carbon atoms, $R^3$ is hydrogen or alkyl of 1–5 carbon atoms and R is hydrogen or $COR^3$ where $R^3$ is as defined above.

4. A compound as claimed in claim 1, which is 4-acetamido-2-methoxythiazole.

5. A compound as claimed in claim 1, which is 4-acetamino-2-ethoxythiazole.

6. A compound as claimed in claim 1, which is 4-acetamido-2-methoxy-5-methylthiazole.

7. A compound as claimed in claim 1, which is 4-diacetylamino-2-methoxythiazole.

8. A compound as claimed in claim 1, which is 4-acrylamido-2-methoxythiazole.

9. A compound as claimed in claim 1, which is 2-methoxy-4-(N-methylacetamido)thiazole.

10. A pharmaceutical composition for use in the treatment of ulcers or hypersecretion which comprises a therapeutically effective amount of a compound as claimed in claim 1 and a pharmaceutically acceptable carrier.

11. A pharmaceutical composition as claimed in claim 1, in unit dosage form.

12. A method of treating ulcers or hypersecretion in an afflicted mammal which method comprises orally administering to said mammal a therapeutically effective amount of a compound of formula I as defined in claim 1.

* * * * *